United States Patent
Mrotzek et al.

(10) Patent No.: US 6,994,545 B2
(45) Date of Patent: Feb. 7, 2006

(54) MULTICOLOR TOOTH USED AS A LAYERING MODEL IN PREPARING VENEERS

(75) Inventors: Olaf Mrotzek, Wasserburg (DE); Novica Savic, Ranstadt (DE)

(73) Assignee: Heraeus Kulzer GmbH & Co. KG, Hanau (DE)

(*) Notice: Subject to any disclaimer, the term of this patent is extended or adjusted under 35 U.S.C. 154(b) by 241 days.

(21) Appl. No.: 10/278,117

(22) Filed: Oct. 22, 2002

(65) Prior Publication Data

US 2003/0180687 A1 Sep. 25, 2003

(30) Foreign Application Priority Data

Nov. 26, 2001 (DE) .......................... 101 57 632

(51) Int. Cl.
*A61C 19/10* (2006.01)

(52) U.S. Cl. ...................... 433/26; 433/203.1

(58) Field of Classification Search .............. 433/203.1, 433/26
See application file for complete search history.

(56) References Cited

U.S. PATENT DOCUMENTS

| 4,115,922 A | | 9/1978 | Alderman ................. 32/71 |
| 4,828,117 A | * | 5/1989 | Panzera et al. ............ 206/63.5 |
| 5,240,414 A | | 8/1993 | Thompson .................. 433/26 |
| 5,624,262 A | * | 4/1997 | Yarovesky et al. ......... 433/223 |
| 5,725,372 A | * | 3/1998 | Leon .......................... 433/26 |
| 5,906,490 A | * | 5/1999 | Kramer Primus et al. ........... 433/203.1 |
| 5,989,031 A | | 11/1999 | Kura et al. ............... 433/202.1 |
| 2002/0049082 A1 | | 4/2002 | Bansemer et al. ............ 433/26 |
| 2002/0081547 A1 | | 6/2002 | Kerschbaumer ............ 433/26 |

FOREIGN PATENT DOCUMENTS

| DE | 34 29 927 A1 | 2/1986 |
| DE | 38 27 657 A1 | 2/1990 |
| DE | 40 24 505 A1 | 2/1992 |
| DE | 44 26 994 A1 | 2/1995 |
| DE | 195 00 658 C2 | 7/1996 |
| DE | 196 54 055 A1 | 6/1998 |
| EP | 1 155 663 A2 | 11/2001 |

* cited by examiner

*Primary Examiner*—Cary E. O'Connor
(74) *Attorney, Agent, or Firm*—Norris McLaughlin & Marcus PA

(57) ABSTRACT

Model tooth for purposes of orientation in dental technical procedures, in which the natural, ordinary layering of neck material, dentin, and enamel is realized using three highly contrasting, translucent materials of different colors that can be distinguished from one another, in a ratio of 1:1.

3 Claims, 1 Drawing Sheet

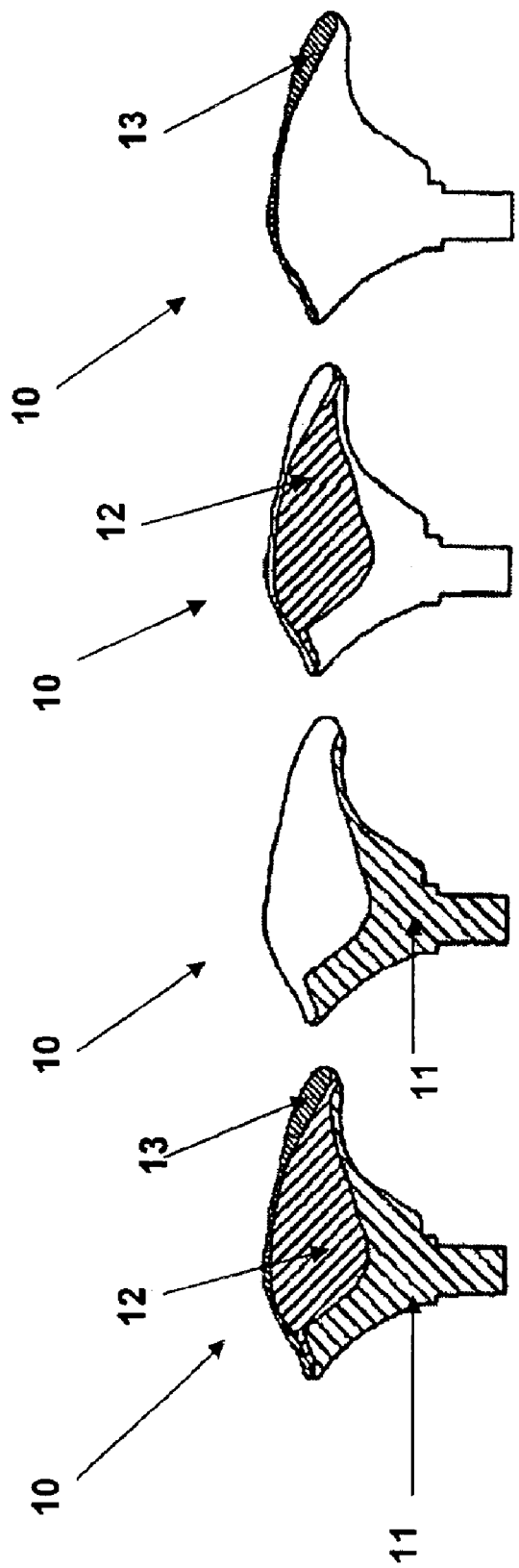

MULTICOLOR TOOTH USED AS A LAYERING MODEL IN PREPARING VENEERS

The invention relates to a model tooth used by dental technicians for orientation while preparing artificial teeth or crowns. The model tooth is based on the layout of the neck material, dentin, and enamel of the natural counterpart in terms of dimensions and, if applicable, translucence, but the layers are colored in highly contrasting shades to allow the layering to be identified, and thus duplicated by the dental technician preparing the artificial tooth or crown.

Natural tooth layers are irregular because layer thickness, and the shape of the layers can be curved to a greater or lesser degree. A natural tooth is comprised essentially of three materials, the neck material, the dentin, and the enamel. The irregularity of the layering is evidenced, for example, in the progression of the translucence in incisors: Along the margins, where the enamel is thick and the layer of dentin is thin, the translucence is high, while it tapers off toward the gums where the layer of dentin is thicker. Here it is entirely possible for the layer of enamel to be somewhat thinner.

In the preparation of artificial teeth and veneer set on metal crowns, it is important for the tooth to look as natural as possible, especially if it is directly next to natural teeth.

Dental technicians have a number of known means at their disposal for generating this natural appearance. Metal cores are coated with opaque layers, after which the tooth is constructed by applying further layers, the color and translucence of which can be selected from a palette. The materials ordinarily used for this include ceramic or readily hardening plastic or composite materials.

The dental technician usually attempts to duplicate the natural course of the layering, to the greatest possible extent, without employing any special materials.

In order to make it easier for technicians to duplicate natural layering, a model tooth was developed to allow dental technicians to see precisely how thick each layer is in each position in the tooth.

The use of model teeth in dental preparations is known in the art. DE 38 27 657 describes a layered model tooth in which the natural tooth is duplicated in terms of hardness and coloration. Radiocontrast agents may also be added. DE 195 00 658 provides for a colored marking of the layers, made visible only afterward, after the preparation exercise, for example via UV light.

By contrast, in the present invention the natural, ordinary progression of the layers in the model tooth is realized with three highly contrasting, translucent materials of different colors that can be distinguished from one another, in a 1:1 ratio. It is also advantageous if the translucence of each of the materials corresponds essentially to that of the natural tooth. However, translucence may also be duplicated via the selection of the colors in the layering.

BRIEF DESCRIPTION OF THE DRAWINGS

FIG. 1 shows the model for an incisor, in which blue material is used for the neck material, uellow material is used for hte dentin, and black, smoke, or anthractie colored material is used for the enamel (illustrated with hatching form the bottom toward the top).

FIG. 2 shows the dental neck material,

FIG. 3 shows the dentin, and

FIG. 4 shows the enamel or cutting material.

"As shown in the figures, in model tooth 10, the natural, average layers of neck material 11, dentin 12 and enamel 13 are realized using three highly contrasting, translucent materials of different colors that can be distinguished from one another, as shown by the hatching".

The model tooth illustrated here appears blackish to gray in places where the layer of enamel is very thick, greenish-gray where little enamel, a thinner layer of dentin and below that the blue neck material show through, and more dull yellow in places where the dentin is very thick. The layering is easier to identify if a light source is positioned behind the tooth. It is also possible to view the tooth using an overhead light, thus allowing a better assessment of the outer layer of enamel. In selecting the colors for the individual layers, manufacturers are limited only by the fact that each layer must be distinguishable from the others. In this context, black and white are considered colors.

What is claimed is:

1. Model tooth used for orientation in dental procedures, comprising a model tooth in which the natural, average layers of neck material, dentin, and enamel are realized using three highly contrasting, translucent materials of different colors that can be distinguished from one another, in a ratio of 1:1, each of the colors and the layers being distinguishable from each other color and layer.

2. Model tooth according to claim 1, in which the neck material is colored blue, the dentin yellow, and the enamel gray or black.

3. Model tooth according to claim 1, in which the translucence of each of the materials corresponds to that of its natural counterpart.

* * * * *